(12) United States Patent
Barry

(10) Patent No.: US 7,670,358 B2
(45) Date of Patent: Mar. 2, 2010

(54) SYSTEM AND METHOD FOR ALIGNING VERTEBRAE IN THE AMELIORATION OF ABERRANT SPINAL COLUMN DEVIATION CONDITIONS

(76) Inventor: Mark A. Barry, P.O. Box 60150, Las Vegas, NV (US) 89160-0150

( * ) Notice: Subject to any disclaimer, the term of this patent is extended or adjusted under 35 U.S.C. 154(b) by 1157 days.

(21) Appl. No.: 11/027,026

(22) Filed: Dec. 30, 2004

(65) Prior Publication Data

US 2006/0149236 A1 Jul. 6, 2006

(51) Int. Cl.
  *A61B 17/88* (2006.01)
(52) U.S. Cl. .................................... 606/279
(58) Field of Classification Search ............ 606/60–61, 606/279, 264, 265, 105, 86
  See application file for complete search history.

(56) References Cited

U.S. PATENT DOCUMENTS

| | | | |
|---|---|---|---|
| 5,102,412 A | 4/1992 | Rogozinski | |
| 5,112,332 A | 5/1992 | Cozad et al. | |
| 5,116,334 A | 5/1992 | Bahr | |
| 5,181,917 A | 1/1993 | Rogozinski | |
| 5,306,275 A | 4/1994 | Schmidt | |
| 5,498,262 A | 3/1996 | Schmidt | |
| 5,545,166 A | 8/1996 | Howland | |
| 5,630,816 A | 5/1997 | Leonardo | |
| 5,676,665 A | 10/1997 | Leonardo | |
| 5,772,661 A | 6/1998 | Michelson | |
| 5,810,817 A | 9/1998 | Tucker | |
| 5,928,232 A | 7/1999 | Howland et al. | |
| 5,947,965 A | 9/1999 | Bryan | |
| 6,015,409 A | 1/2000 | Jackson | |
| 6,090,113 A * | 7/2000 | Le Couedic et al. | ........... 606/61 |
| 6,267,765 B1 | 7/2001 | Taylor et al. | |
| 6,375,657 B1 | 4/2002 | Doubler et al. | |
| 6,440,132 B1 | 8/2002 | Davis | |
| 6,458,131 B1 | 10/2002 | Ray | |
| 6,558,390 B2 | 5/2003 | Cragg | |
| 6,652,526 B1 | 11/2003 | Arafiles | |
| 6,743,231 B1 | 6/2004 | Gray et al. | |
| 6,749,614 B2 | 6/2004 | Teitelbaum et al. | |
| 6,802,844 B2 | 10/2004 | Ferree | |
| 6,821,277 B2 | 11/2004 | Teitelbaum | |
| 6,827,719 B2 | 12/2004 | Ralph et al. | |
| 2006/0195092 A1* | 8/2006 | Barry | ........................ 606/61 |

OTHER PUBLICATIONS

Richard P. Schlenk, M.D., Robert J. Kowalski, M.D., P.E., and Edward C. Benzel, M.D. Biomechanics of spinal deformity, Neurosurg Focus 14 (1);Article 2, 2003.

* cited by examiner

*Primary Examiner*—Eduardo C Robert
*Assistant Examiner*—Elana B Fisher
(74) *Attorney, Agent, or Firm*—Patton Boggs LLP

(57) ABSTRACT

A system and method for ameliorating spinal column anomalies, such as scoliosis, includes bone screws which are to be implanted in the pedicle region(s) of individual to-be-derotated vertebrae and in vertebrae to which balancing forces must be applied as the spinal column is manipulated en mass to achieve an over-all correction of the condition. A pedicle screw cluster derotation tool simultaneously engages multiple pedicle screws and transmits manipulative forces to multiple vertebrae to effect a whole-spine correction. Pre-contoured spinal rods are engaged post-derotation to secure the correction.

5 Claims, 4 Drawing Sheets

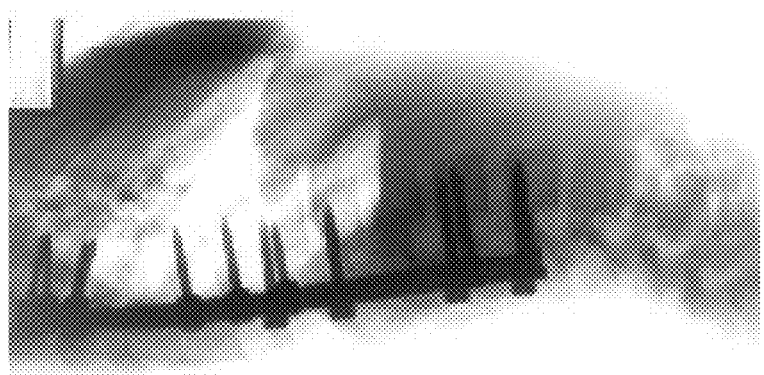
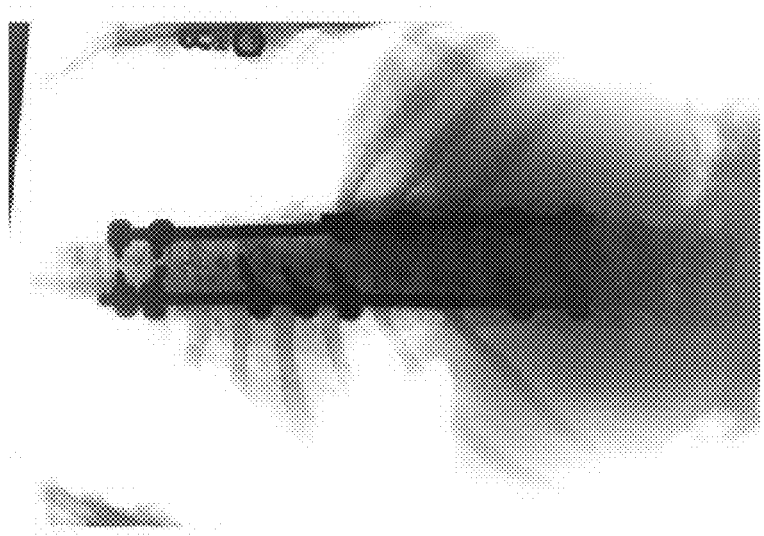
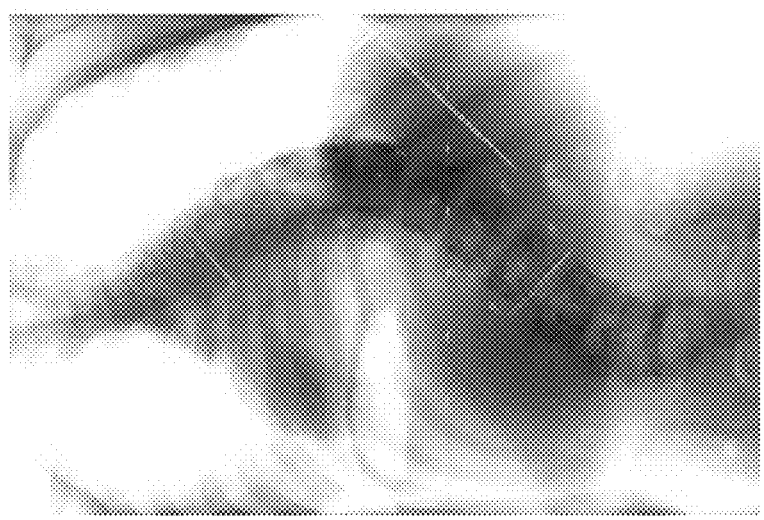
FIG. 6

SYSTEM AND METHOD FOR ALIGNING VERTEBRAE IN THE AMELIORATION OF ABERRANT SPINAL COLUMN DEVIATION CONDITIONS

BACKGROUND OF THE INVENTION

1. Field of the Invention

The present invention relates to methods and apparatus for management and correction of spinal deformities, such as scoliosis.

2. Background Information

A serious deficiency presently exists with respect to conventional treatment and instrumentation for treating spinal deviation anomalies, such as scoliosis.

This circumstance presents a serious medical challenge, because scoliosis, other than mild to moderate cases, is a well-recognized health risk.

If scoliosis curvature exceeds 70 degrees, severe twisting of the spine occurs. This can cause the ribs to press against the lungs, restrict breathing, and reduce oxygen levels. The distortions may also affect the heart and possibly cause dangerous changes.

Eventually, if the curve reaches more than 100 degrees, both the lungs and the heart can be injured. Patients with this degree of severity are susceptible to lung infections and pneumonia. Curves greater than 100 degrees are associated with elevated mortality rates.

Present treatment regimens for scoliosis carry their own risks and side effects, which include:

Spinal fusion disease. Patients who are surgically treated with fusion techniques lose flexibility and may experience weakness in back muscles due to injuries during surgery.

Disk degeneration and low back pain. With disk degeneration, the disks between the vertebrae may become weakened and may rupture.

Height loss.

Lumbar flatback. This condition is most often the result of a scoliosis surgical procedure called the Harrington technique, used to eliminate lordosis (exaggeration of the inward curve in the lower back). Adult patients with flatback syndrome tend to stoop forward. They may experience fatigue and back pain and even neck pain.

Rotational trunk shift (uneven shoulders and hips).

In some patients, years after the original surgery (particularly with the first generation of Harrington rods), the weight of the instrumentation can cause disk and joint degeneration severe enough to require surgery. Treatment may involve removal of the old instrumentation and extension of the fusion into the lower back.

Left untreated, or ineffectively treated, scoliosis carries long-term consequences.

Pain in adult-onset or untreated childhood scoliosis often develops because of posture problems that cause uneven stresses on the back, hips, shoulders, necks, and legs. Studies report, however, that patients with childhood scoliosis have the same incidence of back pain as the general population, which is very high (60% to 80%). In one study conducted 20 years after growth had stopped, two-thirds of adults who had lived with curvatures of 20 to 55 degrees reported back pain. In this study, most cases were mild, although other studies have reported that adults with a history of scoliosis tend to have chronic and more back pain than the general population.

Nearly all individuals with untreated scoliosis at some point develop spondylosis, an arthritic condition in the spine. The joints become inflamed, the cartilage that cushions the disks may thin, and bone spurs may develop. If the disk degenerates or the curvature progresses to the point that the spinal vertebrae begin pressing on the nerves, pain can be very severe and may require surgery. Even surgically treated patients are at risk for spondylosis if inflammation occurs in vertebrae around the fusion site.

The consequences of scoliosis are limited to the physical realm. The emotional impact of scoliosis, particularly on young girls or boys during their most vulnerable years, should not be underestimated. Adults who have had scoliosis and its treatments often recall significant social isolation and physical pain. Follow-up studies of children with scoliosis who did not have strong family and professional support often report significant behavioral problems.

Older people with a history of scoliosis, even those whose conditions were corrected, should realize that some negative emotional events in adulthood may possibly have their roots in their early experiences with scoliosis. Many studies have reported that patients who were treated for scoliosis have limited social activities and a poorer body image in adulthood. Some patients with a history of scoliosis have reported a slight negative effect on their sexual life. Pain appears to be only a minor reason for such limitation. An early Scandinavian study reported that adults with scoliosis had fewer job opportunities and a lower marriage rate than the general population.

It is clear, then, that scoliosis treatment options are presently lacking, and untreated scoliosis (except for mild to lower-moderate cases) is not an acceptable alternative.

There are many apparatus which are designed for attachment to, and positioning adjacent the spinal column, and in many instances, these apparatus are designed for use in treating spinal column anomalies, such as scoliosis. However, all known systems are limited by their design and known implementation modes on either arresting further deleterious rotation of the involved vertebrae, or fixing individual vertebrae once, by some means, they are brought to approximate a desired orientation and position.

Significant correction of severe scoliotic curvature to the point of approximating normal spinal configuration, particularly by a single process, is simply unknown in the art. This is, it is believed, the result of focus in the field on the positioning substantially seriatim of affected vertebrae. Applying derotational force to a vertebrae in this manner cannot effect en mass spinal reconfiguration without risking vertebral fracture at the point of spinal instrumentation fixation, particularly when using conventional instrumentation. Scoliosis has classically been regarded as principally a two dimensional deformity. Early methods of surgical correction have thus focused on two dimensional straightening of the classic S-shaped deformity. Over the last decade or so, more focus has been placed on the true three dimensional deformity. The third dimension is axial plane vertebral rotational deviation maximally affecting the apex of the scoliotic curve. A complete three dimensional correction has become the perceived goal of spine surgeons. There are no existing methods which consistently and reproducibly achieve this goal. Furthermore, significant, focused force applied to any individual vertebra risks spinal cord and related injury. Thus, only force which is inadequate to effect substantial correction to the entire spinal column is thus far ever applied, and correction of scoliotic curvatures are substantially limited.

It has become clear to the present inventor that desired levels of correction of spinal column anomalies, such as scoliosis, can only be achieved if the spinal column (or an affected segment thereof) is manipulated (or "derotated") substantially as a whole into a desired configuration. To achieve such an objective, force must be applied safely to all to-be-derotated vertebrae, and the forces necessary to reconfigure all, or at least a substantial portion of the spinal column must be dispersed throughout the affected spinal segments or regions. Nothing in the prior art satisfies these requirements, either individually or in combination.

SUMMARY OF THE INVENTION

In view of the foregoing, it is an object of the present invention to provide an improved system of spinal instrumentation for use in ameliorating aberrant spinal column deviation conditions, such as scoliosis.

It is another object of the present invention to provide an improved method for ameliorating aberrant spinal column deviation conditions, such as scoliosis.

It is another object of the present invention to provide an improved system of spinal instrumentation, and a method for the use thereof, for ameliorating aberrant spinal column deviation conditions, such as scoliosis, which system and method facilitates the application of significant derotational forces to individual vertebra, with substantially reduced risk for fracture thereof upon application of such forces.

It is another object of the present invention to provide an improved system of spinal instrumentation, and associated method for use thereof, in ameliorating aberrant spinal column deviation conditions, such as scoliosis, which system and method facilitates the application of forces to vertebrae of affected spinal column segments en bloc, thereby distributing otherwise potentially injurious forces in a manner for safely achieving over-all spinal column correction or derotation.

Applicant's present invention provides a system and method for use of such system which satisfy each of these objectives. Applicant's system includes bone screws which are to be implanted in the pedicle region(s) of individual to-be-derotated vertebrae. In the preferred mode of the present invention, such bone screws are also to be implanted in vertebrae to which balancing forces must be applied as the spinal column is manipulated en mass to achieve an over-all correction of the condition. The pedicle implantation provides a stable foundation for the application of significant derotational forces, but without undue risk of vertebral fracture.

The system includes a pedicle screw cluster derotation tool. This tool, in the presently preferred embodiment includes shafts, extending from a common handle or linked handle array, which are oriented and configured to extend to and engage the heads of a number of implanted pedicle screws which will have been implanted in adjacent vertebrae to which derotational or balancing forces are to be applied during a spinal column derotation and alignment. The engagement between the pedicle screw cluster derotation tool and the individual pedicle screws is such that, as manipulative forces are applied to the handle means of pedicle screw cluster derotation tool, forces are transferred and dispersed simultaneously among the engaged vertebrae. Therefore, a practitioner may, in a single motion, simultaneously and safely derotate multiple vertebrae of an affected spinal segment (as well as likewise apply balancing forces to other group(s) of vertebrae which are contiguous to the effected segment(s).

The effect of practice of the present invention is three-dimensional correction which provides, not only spinal correction to near normal configuration, but corrects "rib humps."

The system of the present invention also includes, in its preferred embodiment, pedicle screws which allow for interfacing with, and fixation relative to pre-contoured spinal rods after a satisfactory derotation.

The present inventor's approach to the problems described above is certainly simple, when viewed in hindsight, but it is equally unobvious. In investigative procedures, the presently proposed system and method has achieved measure of correction of scoliotic curvature never before seen in orthopaedic practice.

BRIEF DESCRIPTION OF THE DRAWINGS

The present invention may be more easily understood with reference to figures, which are as follow:

FIG. 6 is a three frame x-ray view showing "before and after" views of a scoliosis patient who was treated in an investigational procedure using the system and method of the present invention. The curvature correction was substantially to normal, and lumbar motion was preserved notwithstanding. Reducing the number of lumbar discs included in the fusion is another advantage of this method over others.

DETAILED DESCRIPTION OF THE PREFERRED EMBODIMENT

With reference to FIGS. 1-4, the spinal deviation correction system of the present invention includes a number of pedicle screws 10, each implanted in respective vertebrae to which rotative forces will be applied in a spinal anomaly correction.

Pedicle screws 10 may be of a variety of designs, such as, for example, are generally depicted in U.S. Pat. Nos. 6,743,237 (Gray, et al), 6,827,719 (Ralph, et al), 6,652,526 (Arafiles), 6,375,657 (Doubler, et al), the disclosures of which are incorporated herein by reference.

Figure 3:
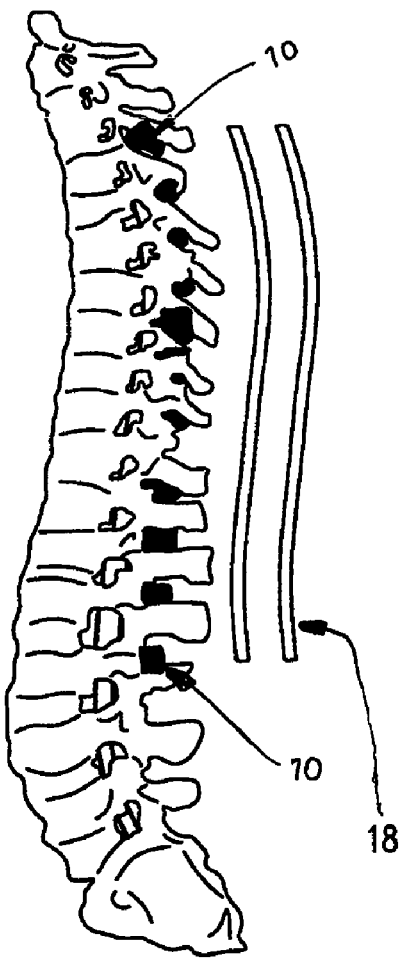
FIG. 3 is an elevational side view of the anatomical model of a human spinal column depicted in FIGS. 1 and 2, with an unobstructed view of already-implanted pedicle screws and adjacent, pre-contoured spinal rods which will be engaged with the pedicle screws through practice of the proposed method.
Figure 4:
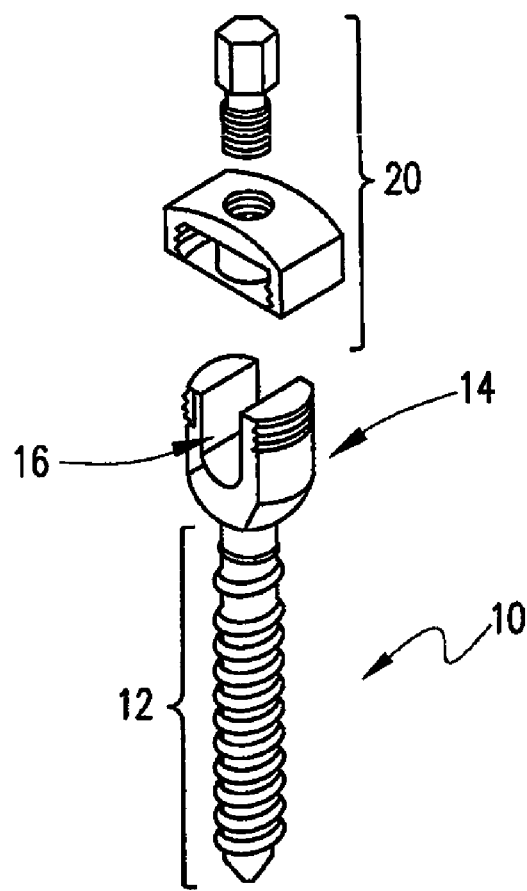
FIG. 4 is an example of a pedicle screw which may be used in the system of the present invention.

With particular reference to FIG. 4, pedicle screws 10 will include a threaded shank segment 12 and a head segment 14. Head segment 14 will be configured with a spinal rod conduit (or channel) 16 or interfacing with a spinal rod 18 (shown in FIG. 3). Spinal rod engagement means 20 serve to fix pedicle screw 10 and spinal rod 18 in relative position and orientation, once a spinal column derotation is complete.

Figure 1:
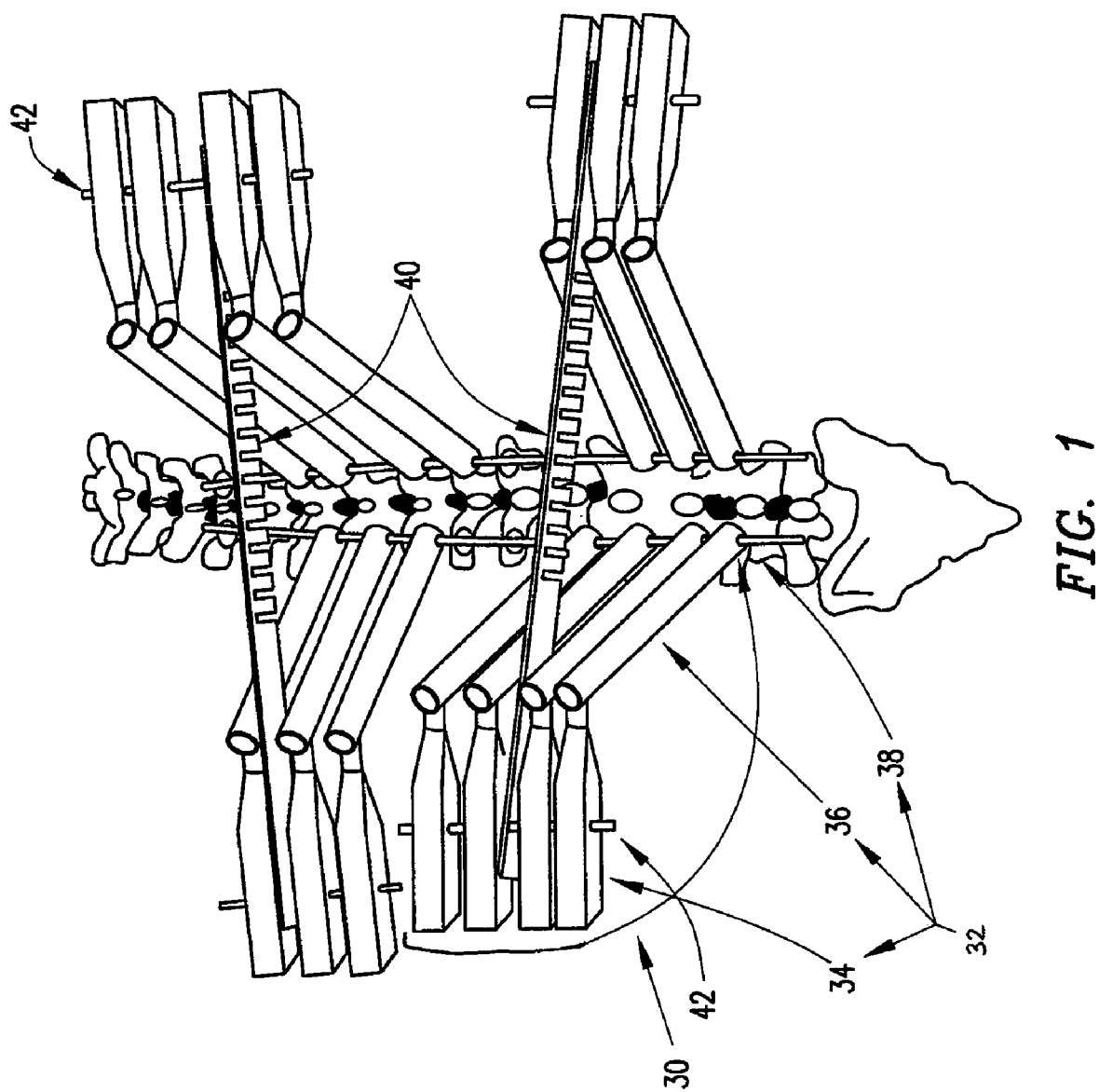
FIG. 1 is a top plan view of an anatomical model of a human spinal column, with components of the system of the present invention shown engaged therewith. The event depicted is that stage of the proposed method after which derotational and balancing forces have been applied to substantially correct a scoliotic curvature.
Figure 2:
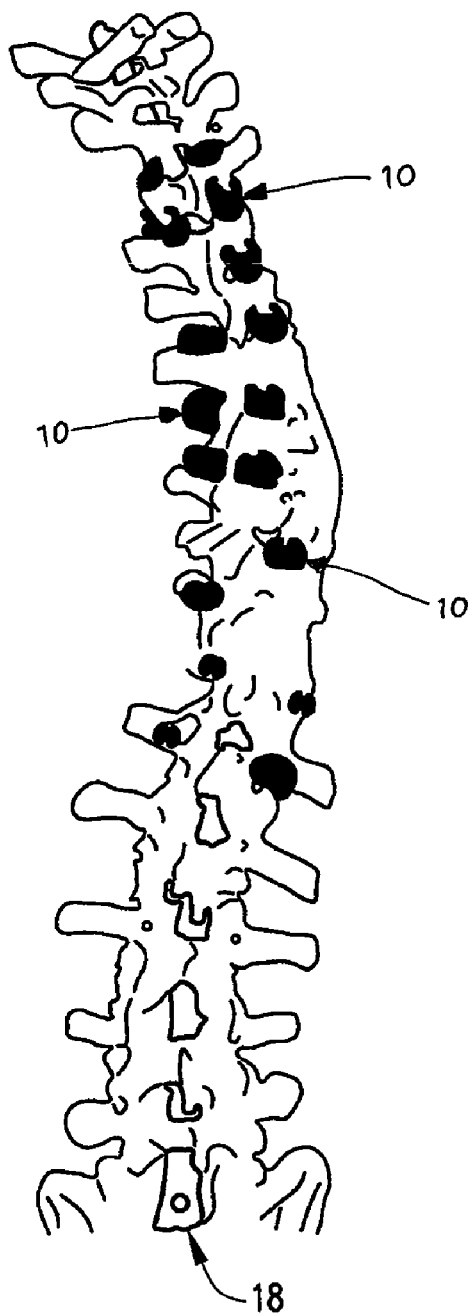
FIG. 2 is an elevational dorsal view of the anatomical model of a human spinal column depicted in FIG. 1, but with an unobstructed view of already-implanted pedicle screws, and configured as if preceding the derotation step of the proposed method.

Referring again, generally to FIGS. 1-4, the system of the present invention further includes a pedicle screw cluster derotation tool 30. As depicted in FIG. 1, each pedicle screw cluster derotation tool 30 is configured from a grouping of pedicle screw wrenches 32, joined together by pedicle screw wrench linking members 42 to act in unison during use (movement to effect a derotation, or application of balancing forces being left to right, or vice versa, as viewed in FIG. 1). Ordinarily, two tools 30 will be involved on either side of the spinal column, with two pedicle screws 10 being implanted in each vertebrae, as shown. Wrench cross linking members 40 are used to coordinate forces applied to screw clusters on either side of the spinal column.

Each pedicle screw wrench 32 includes a handle 34, a shaft 36, and a distal end 38 which is configured to reversibly engage the head segment 14 of a pedicle screw 10 such that, as shaft 36 is moved while shaft distal end 38 is engaged with head segment 14, manipulative forces are transferred to the pedicle screw 10 and, in turn, to the vertebra in which such pedicle screw 10 is implanted.

Significant variations of pedicle screw cluster derotation tool 30 are contemplated by the present invention. For example, the linked, multiple wrenches 32 depicted in FIG. 1 may be replaced by a single handle member from which extend the functional equivalent of the multiple shafts 36 and shaft distal ends 38 for simultaneously engaging multiple pedicle screws 10, as depicted. However configured, the object and design of pedicle screw cluster derotation tool 30 is to facilitate simultaneous application of manipulative forces to multiple pedicle screws 10 which are implanted in a like number of vertebra (a "cluster"). This has the effect of permitting the gross, en bloc application of sufficient derotative forces to affected segments of the spinal column in a sufficiently dispersed manner as to avoid injury to any one vertebra or isolated spinal column segment. This, in turn, facilitates a successful entire-spine, 3D derotation of a scoliosis patient to near normal parameters.

Figure 5:
FIG. 5 is a depiction of the complimentary forces applied to multiple spinal column segments to achieve an over-all spinal column correction.

With reference to FIGS. 1-3 and 5, the preferred mode of the present method usually involves, to achieve an over-all spinal column correction, application of forces to multiple spinal column segments with pedicle screw clusters being accordingly implanted. For example, as depicted in FIG. 5, in the case of a single curvature case of scoliosis, both derotative forces (illustrated by the central force vector arrow of FIG. 5) to vertebrae involved in scoliotic curvatures, as well as of balancing, or offsetting forces to contiguous spinal segments cephalad and caudad (illustrated by the lateral arrows of FIG. 5) are applied.

The preferred mode of the present method involves precontouring spinal rods 18, as shown in FIG. 3. The spinal rod(s) 18 are engaged with pedicle screws 10, and, after the manipulative forces are applied to pedicle screw cluster derotation tool(s) 30, the spinal rod engagement means 20 is tightened to fix pedicle screw 10 and spinal rod 18 in relative position and orientation to secure the corrected spinal column configuration. Spinal rod engagement means 20 of pedicle screws 10 are tightened, using an anti-torque feature of wrenches 32 (or of their equivalent in an alternative embodiment). This feature, as is well known in the art, allows tightening of nuts and the like, without imparting undue torque to the underlying apparatus or structure.

As shown in FIG. 6, investigative practice of the present method achieves efficacy never before seen in the orthopaedic field. The "before picture" is the left hand image of FIG. 6, and the two remaining images are sagittal and dorsal views of the corrected spinal column.

Although the invention has been described with reference to specific embodiments, this description is not meant to be construed in a limited sense. Various modifications of the disclosed embodiments, as well as alternative embodiments of the inventions will become apparent to persons skilled in the art upon reference to the description of the invention. It is, therefore, contemplated that the appended claims will cover such modifications that fall within the scope of the invention.

I claim:

1. A method for aligning vertebrae in the amelioration of aberrant spinal column deviation conditions comprising the steps of:

selecting a first set of pedicle screws, said pedicle screws each having a threaded shank segment and a head segment;

selecting a first pedicle screw cluster derotation tool, said first pedicle screw cluster derotation tool having first handle means and a first group of pedicle screw engagement members which are mechanically linked with said first handle means, each pedicle screw engagement member being configured for engaging with, and transmitting manipulative forces applied to said first handle means to said head segment of each pedicle screw of said first set of pedicle screws, implanting a each pedicle screw in a pedicle region of each of a first group of multiple vertebrae of a spinal column which exhibits an aberrant spinal column deviation condition;

engaging each pedicle screw engagement member respectively with said head segment of each pedicle screw of said first set of pedicle screws; and applying manipulative force to said first handle means in a manner for simultaneously engaging said first group of pedicle screw engagement members and first set of pedicle screws and thereby in a single motion simultaneously rotating said vertebrae of said first group of multiple vertebrae in which said pedicle screws are implanted to achieve an amelioration of an aberrant spinal column deviation condition;

selecting a first length of a spinal rod member; wherein one or more of said pedicle screws of said first set of pedicle screws each includes:

a spinal rod conduit formed substantially transverse of the length of said pedicle screw and sized and shaped for receiving passage of said spinal rod member therethrough; and spinal rod engagement means for securing said pedicle screw and said spinal rod member, when extending through said spinal rod conduit, in a substantially fixed relative position and orientation;

extending said first length of said spinal rod member through said spinal rod conduits of one or more of said pedicle screws of said first set of pedicle screws; and after applying said manipulative force to said first handle means, actuating said spinal rod engagement means to secure said vertebrae in their respective and relative positions and orientations as achieved through application of said manipulative force thereto.

2. The method of claim 1 further comprising the steps of:

selecting a second set of pedicle screws;

selecting a second pedicle cluster derotation tool, said second pedicle screw cluster derotation tool having second handle means and a second group of pedicle screw engagement members which are mechanically linked with said second handle means, each pedicle screw engagement member being configured for engaging with, and transmitting manipulative forces applied to said second handle means to said head segment of each pedicle screw of said second set of pedicle screws, implanting each pedicle screw in a pedicle region of each of a second group of multiple vertebrae of a spinal column which exhibits an aberrant spinal column deviation condition;

engaging each pedicle screw engagement member respectively with said head segment of each pedicle screw of said second set of pedicle screws; and applying manipulative force to said second handle means in a manner for simultaneously engaging said second group of pedicle screw engagement members and said second set of pedicle screws and thereby in a single motion simultaneously rotating said vertebrae of said second group of multiple vertebrae in which said pedicle screws are implanted to achieve an amelioration of an aberrant spinal column deviation condition.

3. The method of claim 2 further comprising the steps of:

selecting a second length of a spinal rod member, wherein one or more of said pedicle screws of said second set of pedicle screws each includes:

a spinal rod conduit formed substantially transverse of the length of each said pedicle screw and sized and shaped for receiving passage of said spinal rod member therethrough; and spinal rod engagement means for securing said pedicle screw and said second spinal rod member, when extending through said spinal rod conduit, in a substantially fixed relative position and orientation;

extending said second length of said spinal rod member through said spinal rod conduits of one or more of said pedicle screws of said second set of pedicle screws; and after applying said manipulative force to said second handle means, actuating said spinal rod engagement means to secure said vertebrae of said second group of multiple vertebrae in their respective and relative positions and orientations as achieved through application of said manipulative force thereto.

4. The method of claim 3 wherein the steps of applying manipulative force to said first handle means and applying manipulative force to said second handle means are carried out substantially simultaneously to cooperatively achieve an amelioration of an aberrant spinal column deviation condition.

5. The method of claim 2 wherein the steps of applying manipulative force to said first handle means and applying manipulative force to said second handle means are carried out substantially simultaneously to cooperatively achieve an amelioration of an aberrant spinal column deviation condition.

* * * * *

UNITED STATES PATENT AND TRADEMARK OFFICE
CERTIFICATE OF CORRECTION

PATENT NO. : 7,670,358 B2  Page 1 of 1
APPLICATION NO. : 11/027026
DATED : March 2, 2010
INVENTOR(S) : Mark A. Barry It is certified that error appears in the above-identified patent and that said Letters Patent is hereby corrected as shown below:

Title page, item [56]

References Cited

U.S. PATENT DOCUMENTS - NAMED INVENTORS SHOULD READ AS FOLLOWS:

| | | |
|---|---|---|
| 5,116,334 | 5/1992 | Cozad, et al |
| 5,306,275 | 4/1994 | Bryan |
| 5,498,262 | 3/1996 | Bryan |
| 5,630,816 | 5/1997 | Kambin |
| 5,676,665 | 10/1997 | Bryan |
| 5,810,817 | 9/1998 | Roussouly, et al |
| 6,440,132 | 8/2002 | Jackson |

Signed and Sealed this

Eighteenth Day of September, 2012

David J. Kappos
*Director of the United States Patent and Trademark Office*